United States Patent
Anand et al.

(10) Patent No.: US 9,579,078 B2
(45) Date of Patent: Feb. 28, 2017

(54) EXCITATION SCHEMES FOR LOW-COST TRANSDUCER ARRAYS

(71) Applicant: KONINKLIJKE PHILIPS N.V., Eindhoven (NL)

(72) Inventors: Ajay Anand, Fishkill, NY (US); John Petruzzello, Carmel, NY (US); Shiwei Zhou, Yorktown Heights, NY (US); Rajendra Singh Sisodia, Bhopal (IN); Pallavi Vajinepalli, Bangalore (IN); Lalit Gupta, Noida (IN); Ganesan Ramachandran, Bangalore (IN); Celine Firtion, Surat (IN)

(73) Assignee: Koninklijke Philips N.V., Eindhoven (NL)

(*) Notice: Subject to any disclaimer, the term of this patent is extended or adjusted under 35 U.S.C. 154(b) by 170 days.

(21) Appl. No.: 14/345,823

(22) PCT Filed: Sep. 17, 2012

(86) PCT No.: PCT/IB2012/054910
§ 371 (c)(1),
(2) Date: Mar. 19, 2014

(87) PCT Pub. No.: WO2013/042029
PCT Pub. Date: Mar. 28, 2013

(65) Prior Publication Data
US 2014/0243673 A1    Aug. 28, 2014

Related U.S. Application Data

(60) Provisional application No. 61/537,668, filed on Sep. 22, 2011.

(51) Int. Cl.
A61B 8/00 (2006.01)
A61B 8/06 (2006.01)
(Continued)

(52) U.S. Cl.
CPC .............. *A61B 8/06* (2013.01); *A61B 8/0866* (2013.01); *A61B 8/0891* (2013.01);
(Continued)

(58) Field of Classification Search
CPC ..................................... A61B 5/00; A61B 8/00
(Continued)

(56) References Cited

U.S. PATENT DOCUMENTS 4,530,363 A * 7/1985 Brisken .................... A61B 8/06
                                                    600/455
4,733,562 A    3/1988 Saugeon
(Continued)

OTHER PUBLICATIONS

Karaman et al: "Synthetic Aperture Imaging for Small Scale Systems": IEEE Transactions on Ultrasonics Ferroelectrics and Frequency Control, vol. 42, No. 3, May 1995, PP.

*Primary Examiner* — Joel F Brutus (57) ABSTRACT

A device images time-wise in parallel using transducer elements of a group. The elements are of a current group and imaging is time-wise sequential by group. The groups may be spatially disposed with respect to each other so as to mutually intermesh element-wise. The imaging may include volumetric imaging. The device may be configured for not collectively using any of the elements to focus, nor to steer, a beam used in the imaging. The device may further be operable to transition between spacing states at least one of which is characterized by a respective minimum, nonzero, degree of intra-group, element-to-element non-adjacency, or may be fixed at a selected spacing state. The transitioning may be automatic, in response to input indicative of blood vessel size and/or depth.

17 Claims, 6 Drawing Sheets

(51) Int. Cl.
*G01S 15/89* (2006.01)
*A61B 8/08* (2006.01)
*G01S 7/52* (2006.01)

(52) U.S. Cl.
CPC ............ *A61B 8/4494* (2013.01); *A61B 8/483* (2013.01); *A61B 8/488* (2013.01); *A61B 8/5223* (2013.01); *G01S 7/52085* (2013.01); *G01S 15/8927* (2013.01); *G01S 7/52036* (2013.01); *G01S 7/52077* (2013.01); *G01S 7/52084* (2013.01)

(58) Field of Classification Search
USPC .................................................. 600/437, 447
See application file for complete search history.

(56) References Cited

U.S. PATENT DOCUMENTS

| | | |
|---|---|---|
| 5,997,479 A | 12/1999 | Savord et al. |
| 6,126,602 A | 10/2000 | Savord et al. |
| 2008/0114249 A1 | 5/2008 | Randall et al. |
| 2010/0022883 A1 | 1/2010 | Satoh |
| 2010/0277305 A1 | 11/2010 | Garner et al. |

* cited by examiner

EXCITATION SCHEMES FOR LOW-COST TRANSDUCER ARRAYS

CROSS-REFERENCE TO PRIOR APPLICATIONS

This application is the U.S. National Phase application under 35 U.S.C. §371 of International Application No. PCT/IB2012/054910, filed on Sep. 17, 2012, which claims the benefit of U.S. Provisional Patent Application No. 61/537668, filed on Sep. 22, 2011. These applications are hereby incorporated by reference herein.

FIELD OF THE INVENTION

The present invention relates to excitation schemes for a transducer array and, more particularly, to schemes for operating the array for imaging.

BACKGROUND OF THE INVENTION

Assessing the well being of fetus is a very important clinical practice in pregnancy care. Currently, the most prevalent ways for doctors to assess fetal well-being are the analysis of fetal heart rate using a cardio-tocograph (CTG) and the assessment of maternal and fetal blood vessel flows using ultrasound Doppler. Ultrasound Doppler waveform analysis of specific blood flows of fetus and mother is part of established medical practice, and a standard recommendation in various clinical guidelines for the diagnosis and assessment of high-risk pregnancies (type-2 diabetes, hypertension or pre-eclampsia in mother and IUGR—intra-uterine growth restriction of fetus). One of the main aims of routine antenatal care is to identify the "at risk" fetus in order to clinically intervene, thereby reducing the incidence of perinatal morbidity and mortality. Some of the vessels useful in the assessment of fetal well-being are: the umbilical artery, the middle cerebral artery, the ductus venosus, and the (left and right) uterine arteries and umbilical veins.

Ultrasound scanners have become indispensible in the monitoring of pregnancies worldwide. They currently provide the best option to monitor the growth and development of the fetus. Duplex ultrasound scanners provide ultrasound pulsed wave Doppler in addition to the regular scan. Color and power Doppler are newer additions to the range of scanners that provide for vascular imaging. Color Doppler, in particular, is commonly provided, resulting in what is often called a "triplex" scanner.

Doppler exams typically require a great degree of skill to obtain a clinically useful measurement. For example, correct orientation of the probe with respect to the vessel is essential to ensure that the beam-flow angle is less than 60 degrees. Errors in measurements are amplified when angles of greater than 60 degrees are used in the determination of velocities. The standard workflow on a clinical ultrasound scanner allows a sonographer to determine the orientation of the probe with respect to the vessel using a standard B-mode and Color Flow display. The spectral Doppler measurements are then obtained thus ensuring that the measured velocities are correct.

The use of ultrasound in vascular applications to perform Doppler velocimetry requires availability of skilled personnel.

SUMMARY OF THE INVENTION

In emerging market countries such as India, the shortage of specialists limits the availability and access to ultrasound. Hence, an automated method of acquiring and evaluating Doppler signals for clinical diagnosis (without requiring the user to interpret an ultrasound scan image) would be useful to non-radiologists such as OB/GYN or cardiologists who are the primary treatment providers.

In addition, a low-cost system is essential to provide an attractive solution in emerging market environments. Devices that are currently available in the market for antenatal check-ups and labor are the ultrasound and CTG machines. However, both of these devices are relatively expensive.

There exists a need for low-cost, easy-to-use solution to provide Doppler velocimetry to screen and monitor high risk pregnancies.

Commonly-assigned patent application entitled "Automated Doppler Velocimetry Using a Low-Cost Transducer" discloses a hand-held, stand-alone, Doppler-based, ultrasound probe whose examining face is less finely divided into separate transducer elements, i.e., for relatively few separate elements. As mentioned therein, the probe operates automatically without the need for interpreting a visual display of anatomy.

The present patent application is directed to novel excitation schemes for an array of transducer elements, with particular application to the probe referred to immediately above.

In accordance with the present invention, a device is designed for imaging, time-wise in parallel using transducer elements of a current group, and time-wise sequentially by group. The groups are spatially disposed with respect to each other so as to mutually intermesh element-wise.

In an aspect of the invention, the device is configured not to collectively use any of the elements of the groups to focus, nor to steer, a beam used in the imaging.

In one embodiment, the device includes the elements of the groups.

In another aspect, the device is further configured for varying the grouping.

In a sub-aspect, the varying is based on input indicative of vessel size and/or vessel depth.

In an alternative sub-aspect, the varying includes transitioning between one and another of at least two spacing states. At least one of the states is characterized by a respective minimum, nonzero, degree of element-to-element non-adjacency between elements of a group.

In a sub-aspect of the alternative, the device is configured for the transitioning automatically in response to input indicative of a vessel size and/or a vessel depth.

In a particular aspect, the elements of the current group have respective faces with corresponding geometric centers. The device is configured for a minimum, nonzero degree of element-to-element non-adjacency between the elements of the current group. The minimum is representative of a minimum distance between the geometric centers.

In a sub-aspect, the minimum distance is, for the one or more pairs of the elements of the current group, sufficient to allow some element of another one of the groups to intervene between the pair, with the corresponding geometric centers colinear.

In a second sub-aspect, the minimum distance is, for the one or more pairs of the elements of the current group, sufficient to allow some two elements of another one or more of the groups to intervene between the pair, with the corresponding geometric centers colinear.

In a related aspect, the elements of the current group are pair-wise separated by at least one respective intervening element of another group.

In one other aspect, the groups are element-wise mutually exclusive.

In a different aspect, the elements of the groups are collectively arranged in a multi-dimensional array.

In yet another aspect, the using includes firing the elements of the current group simultaneously.

In still another aspect, the imaging comprises medical imaging.

In an additional aspect, the imaging utilizes a fluid-flow analysis technique.

In yet another aspect, a handheld, stand-alone, diagnostic apparatus comprises the device.

In one version, the device is configured as one or more integrated circuits.

In a yet, different aspect, a device is configured for volumetric imaging by operating transducer elements timewise in parallel and for not collectively using any of the elements to focus, nor to steer, a beam used in the imaging.

In a sub-aspect, the imaging includes performing fluid flow analysis.

Details of the novel device, and its firing schemes, are set forth further below, with the aid of the following drawings, which are not drawn to scale.

DETAILED DESCRIPTION OF EMBODIMENTS

The description of what is proposed herein with regard to transducer excitation schemes is preceded with what largely is a review of the Doppler-based probe disclosed in the patent application "Automated Doppler Velocimetry Using a Low-Cost Transducer." Discussion focusing particularly on the present invention will then commence in connection with FIG. 4 and the subsequent figures.

Figure 1:
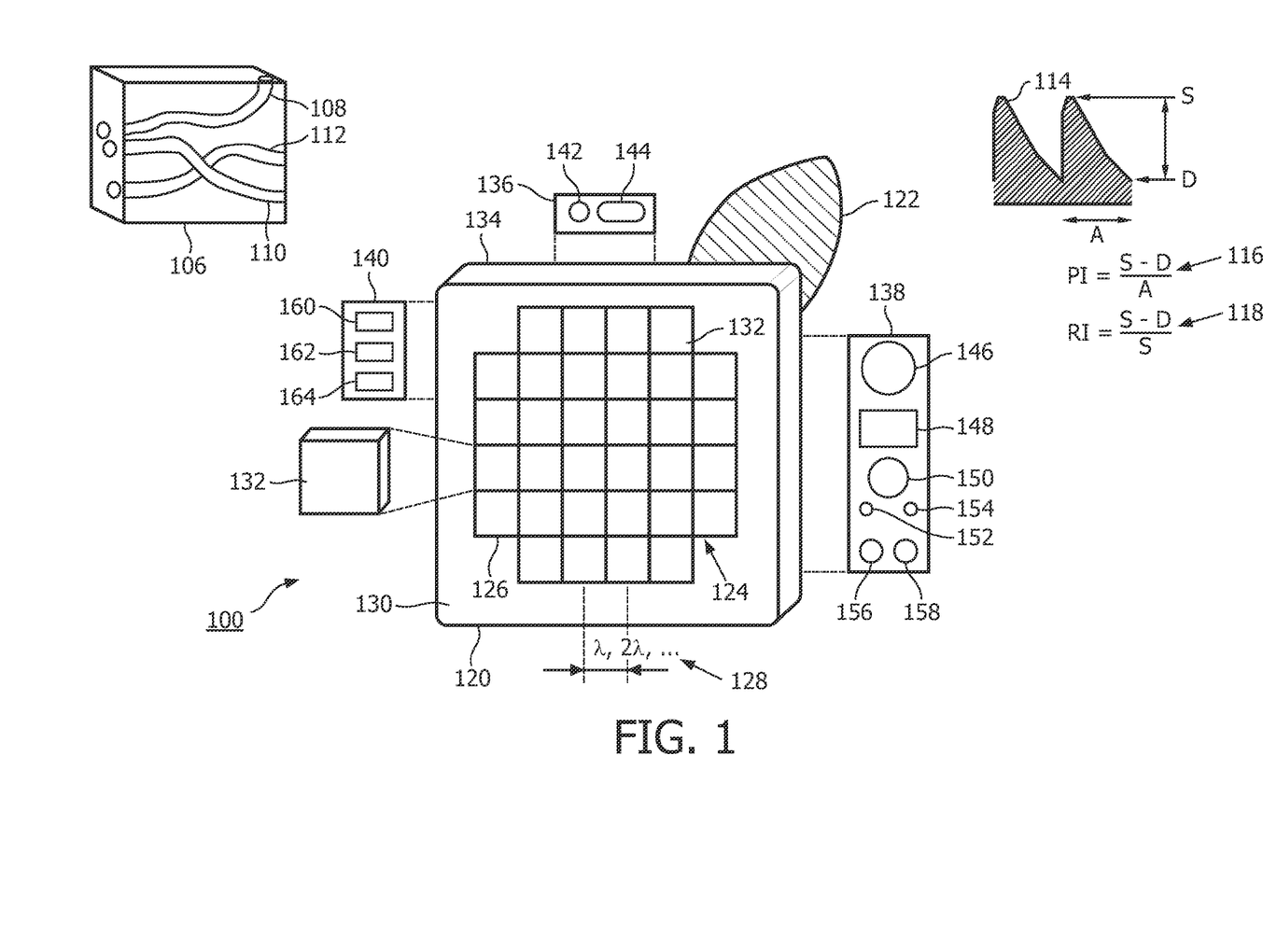
FIG. 1 is a schematic diagram showing, by example, an ultrasound probe, a volume of interest containing blood vessels, and a blood-flow waveform and respective clinical Doppler indices.

FIG. 1 depicts, by way of illustrative and non-limitative example, an ultrasound probe 100 and a volume or "volume of interest" 106 containing blood vessels 108, 110, 112. Further depicted are a blood-flow, or "spectral Doppler ultrasound", waveform 114 and respective clinical Doppler indices 116, 118.

The probe 100 is implementable as an automatic, handheld, stand-alone, self-contained, ultrasound examination device. It has a transducer housing 120 and a handle 122.

Within the transducer housing 120, a non-phased, two-dimensional transducer array 124 is comprised of transducer elements 126, the number of elements being determined by the scan volume and anatomy. Data acquisition occurs individually by element 126, although, as discussed in more detail further below, elements are operable concurrently to shorten the total acquisition time period.

As seen in FIG. 1 by way example, the number of elements 126 is 32. Thus, with an element size of 10 mm, an approximately 6 cm×6 cm volume is covered. Flush with a front surface 130 of the housing 120, are ultrasound-receiving faces 132 of the transducer elements 126, the same faces also transmitting, i.e., issuing, ultrasound.

The total of merely 32 elements 126 stands in stark contrast to the much greater number of elements that would be required in conventional medical imaging to cover the same 6 cm×6 cm volume.

In this regard, electronic focusing for medical imaging, as with a phased-array transducer, requires an inter-element spacing of a ½ wavelength, i.e., ½λ, or less. Doppler ultrasound for imaging can typically range from between $2 \times 10^6$ and $4 \times 10^6$ cycles per second (2 to 4 MHz). Ultrasound travels through soft body tissue at a speed of about 1540 meters/second. Wavelength, i.e., λ, is equal to velocity divided by frequency. Here, this is 1540 ms divided by approximately $2 \times 10^6$ cycle/s=0.8 millimeter. Medical ultrasound imaging for a display would therefore require an inter-element spacing of less than 0.4 mm, and an element surface area of less than $(0.4 \text{ mm})^2$ which is less than 0.2 mm². Therefore, with a small element size on the order of ½λ, thousands of elements 126 would be required to build a 2D array that, like the one seen in FIG. 1, covers a volume of 6 cm by 6 cm.

The spacing (size) of elements in FIG. 1 is 10 mm, which, as discussed above, would ordinarily be more than 12λ of ultrasound used in examining the volume of interest 106 for the blood vessels 108, 110, 112 present.

More generally, the elements 126, in accordance with what is proposed herein, are spaced apart by more than ½λ, although inter-element spacing 128 may be λ, 2λ or more, as discussed hereinabove. The area of the face 132 is, correspondingly, at least 0.6 square millimeters (mm²), and may be more, such as 10 mm², 25 mm², or 100 mm² as in FIG. 1.

Advantageously, the automatic ultrasound device 100 does not rely on display of medical images to reach a diagnosis; but, instead, features an array composed of fewer transducer elements and therefore fewer channels. Thus, cost of production is low, while, by virtue of automatic operation, reliability is maintained. Reliability may even be improved, as when medical examinations must be performed at a quicker pace. The automatic operation also tends to reduce examination time, thereby relieving workload, and making the examination more convenient.

During Doppler data acquisition, the elements 126 are fired either sequentially, or in one or more groups taking care that the acoustic signal from one element does not significantly affect others that are excited at the same time. For each element 126, the receive period lags the transmit period. The Doppler receive gate is correspondingly positioned in the receive period so as to enable sampling from a corresponding depth within the volume of interest 106.

On a back surface 134 of the housing 120, so as to face the user, are a number of user-interface, input-output panels which include a top panel 136, a left panel 138 and a right panel 140. An on-off switch 142 and an audio speaker face 144 are disposed in the top panel 136. The left panel 138 frames a function navigation/actuation button 146, a display 148, a Doppler power detection indicator 150, fetal heartbeat acquisition indicator 152, a maternal heartbeat acquisition indicator 154, a normal blood-flow indicator 156, and an abnormal blood-flow indicator 158. The right panel 140 includes three initializing-parameter-entry feedback windows 160, 162, 164.

The elements 126 of the array 124 all are operated to image independently.

This stands in contrast to phased arrays for example, which use multiple separate transducer elements collectively to image or steer a beam. In phased arrays, the steering and focusing is performed by appropriately delaying the input and/or output of elements with respect to other elements.

In accordance with what is proposed herein, the transducer elements of a group are fired simultaneously. The group elements continue imaging concurrently, and independently by element, until expiration of the group's data acquisition time period.

A device for the imaging by groups is configured not to collectively use any of the elements 126 to focus, nor to steer, a beam used in the imaging. By way of demonstration, the transducer elements 166, 168, 170, 172 in FIG. 1 each have their respective signals 174, 176, 178, 180. The signals 174, 180 on transmit lag the transmission signals 176, 178 thereby resulting in focus and/or steering of a resultant ultrasound beam. The probe is not implemented for such a protocol, as indicated by the "X" 182 in FIG. 1. Likewise, on receive, no delay is differentially applied to the elements 166, 168, 170, 172.

Clinical Doppler indices, such as the pulsatility index (PI) 116 and the resistance index (RI) 118 are Doppler angle-independent measures of blood pulsatility. The symbols S, D and A annotating the blood-flow waveform 114 in FIG. 1 represent, respectively, the peak systolic frequency shift, the end diastolic frequency shift, and one cardiac cycle. The blood-flow waveform 114 is a graph of Doppler frequency, and thus blood flow velocity, versus time.

The probe 100 can utilize both indices PI and RI in identifying blood vessels and in assessing normality of blood flow.

Figure 2:
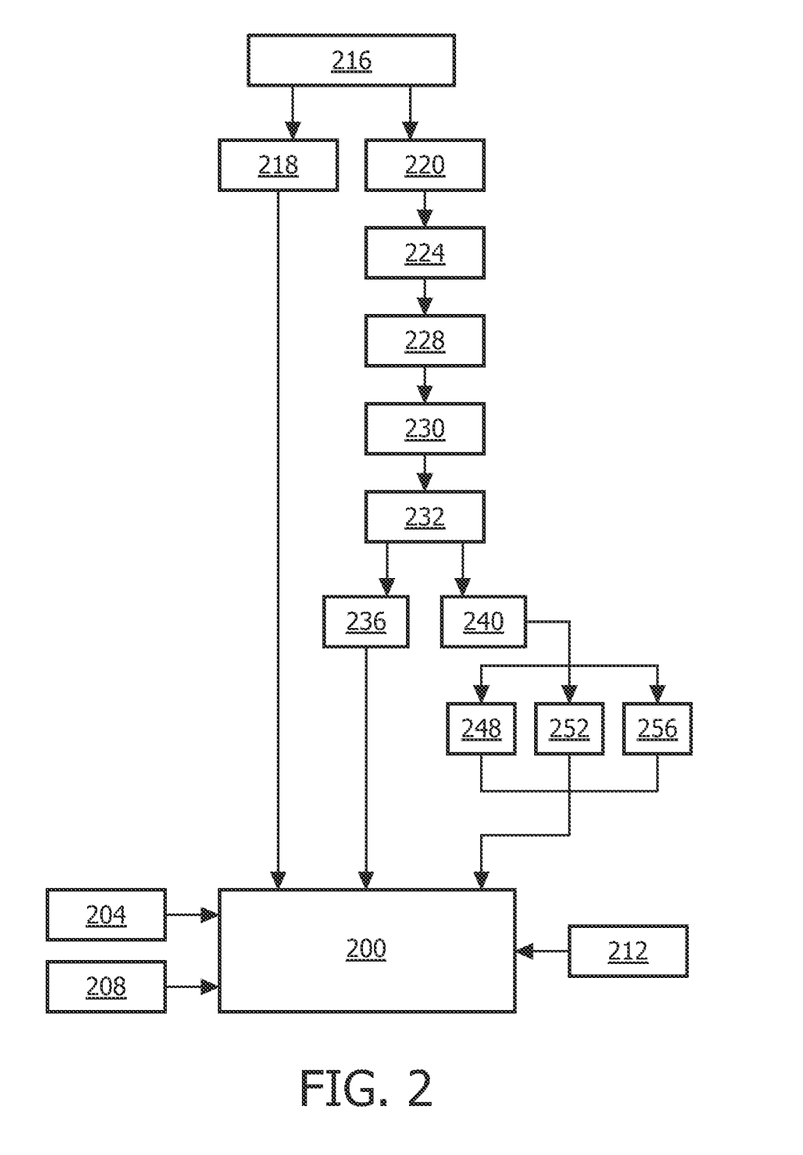
FIG. 2 is a conceptual flow diagram of exemplary signal processing.

The signal processing involved in classifying a blood vessel 108-112 found by the probe 100 in the volume of interest 106 is shown, by example, in FIG. 2.

A blood vessel classifier 200 can be implemented as a k-nearest neighbor (K-NN) classifier, with K=3 for example.

The classifier is first used to predict whether the vessel 108-112 is a vein or artery. Various feature inputs to the classifier 200, such as the PI, are used, each of the M types of input corresponding to a dimension in M-dimensional feature space. Another type of input to the classifier is training examples. Each training example corresponds to an actual clinical case, and includes the M feature inputs for that case, defining the example as a particular point, i.e., "example point", in the M-dimensional space. With each example point is associated the respective outcome of "vein" or "artery", depending upon whether that training example actually pertained to a vein or to an artery. The classifier 200 having been initialized with the training examples, a point in M-dimensional space is formed using the feature inputs derived for the blood vessel 108-112 currently being classified. For K=3, the 3 closest neighbor (example) points are identified. Each neighbor will have as its outcome either the value "artery" or "vein." The majority vote prevails. There are never any ties since 3 is an odd number.

If the vessel is classified as an artery, the classifier 200 next determines whether it is maternal or fetal, by the same nearest neighbor algorithm. If the blood vessel is a maternal artery, a determination is made as to whether it is a uterine artery. If, on the other hand, the vessel is a fetal artery, a determination is made as to whether it is the umbilical artery. The latter two determinations use the same nearest neighbor algorithm.

Nearest neighbor classifiers enjoy the benefit of simplicity, although other alternative methods such as neural networks, or support vector machines (SVMs), could be used instead.

Classifier inputs from the user include the gestational age 204, and a rough, approximate location 208 of the probe on the mother's abdomen. A vascular model 212 in the form of training examples for the classifier 200 is also provided.

Other inputs come directly or indirectly from the pulse-echo information from received ultrasound 216.

Directly from the ultrasound 216, an average reflective index estimation 218 is made for the tissue around the probe 100. This index is compared to a pre-defined reflection index list to determine the position of the probe 100 on the mother's body.

To form indirect inputs, the ultrasound received is demodulated in a demodulator 220 to extract an ultrasound Doppler signal 224 from the carrier frequency. A fast Fourier transform (FFT) 228 is performed on the Doppler signal 224 to generate a spectrogram, or "FFT-based sonogram", 230. From the spectrograms 230, one or more relevant spectral profiles 232 are extracted. The term "spectral profile" signifies the part of the sonogram 230 that corresponds to blood flow through an artery or vein. The spectral profile 232 can be approximated as the region between curves corresponding to the maximum and minimum spectral velocities (or spectral frequencies). The spectral breadth 236 of the extracted spectral profile 232 is estimated and provided to the classifier 200. From the spectral profile(s) 232, a curve 240 corresponding to the peak (or, alternatively, the average) spectral velocities is extracted. Specific temporal features 248 are also extracted from the spectral profile(s) 232. These features include, for example, the presence of a notch immediately preceding the pulse in the blood flow waveform 114 of a uterine artery. The PI and RI for the vessel about to be subject to classification 252 are also extracted. In an initialization procedure which precedes examination of the current volume of interest 106, the pulse cycle time estimation 256 is performed based on the spectral profile(s) 232 then extracted.

Figure 3A:
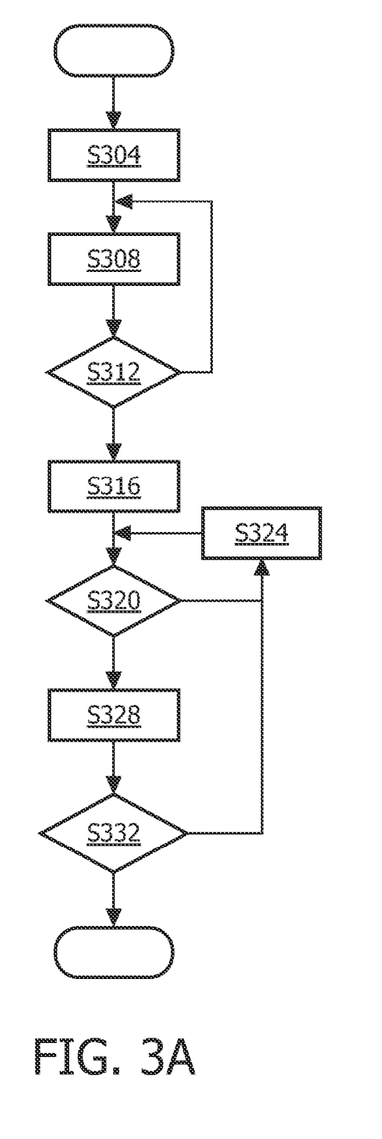
FIGS. 3A and 3B are flow charts demonstrating an example of probe operation.
Figure 3B:
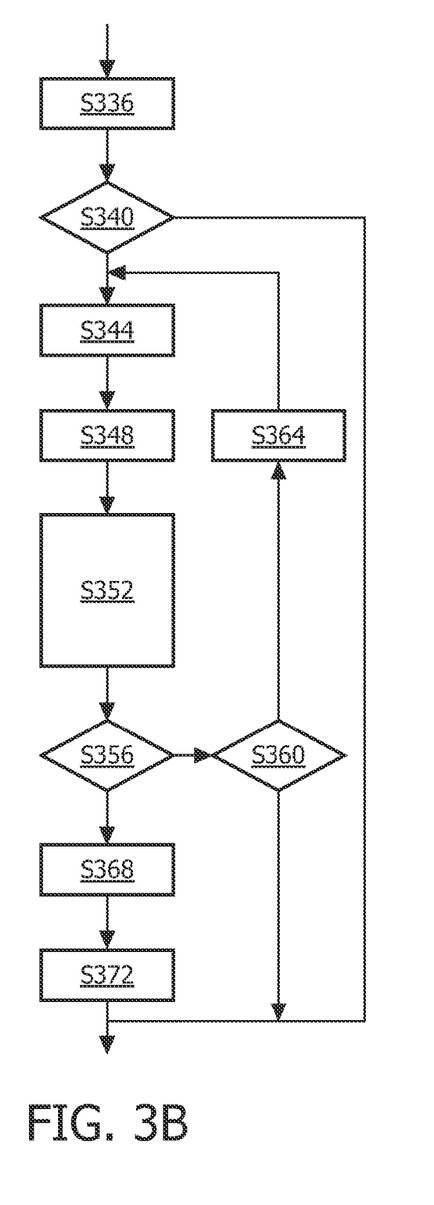

Operationally, and as shown in FIGS. 3A and 3B, the user, who may be a clinician, midwife, general practitioner, obstetrician/gynecologist or fetal radiologist, inputs, as part of the initialization procedure, a target blood vessel for examination, e.g., left uterine artery (falling within the "uterine artery" blood-vessel physiological category); gestational age; and a rough description of the location the probe will have once initialization ends and the examination begins. Specifically, after actuating the on/off switch 142, the user presses the function navigation/actuation button 146 twice in succession quickly. In response, the first blood vessel choice appears in the display 148. If the choice appearing is not the target blood vessel for examination, the button 146 is pressed once to bring up a new choice in the display 148. This is done repeatedly until the choice displayed is the one for selection. The button 148 is then held down, and the choice is echoed in the initializing-parameter-entry feedback windows 160. Appearing in the display 148 is a choice for gestational age, in months or weeks. In a similar fashion, the user navigates to the correct age, and holds down the button 146, to echo the selection to the window 162. To complete initializing-parameter entry, the same procedure is carried out for the probe location, the selected location being shown in the window 164. Optionally, more than one target blood vessel can be designated.

These can be processed in the order in which they are found, or a particular order can be specified during this initialization (step S304).

The user now continues with initialization by placing the probe on the mother's abdomen for pulse cycle time estimation 256. The user presses the function navigation/actuation button 146 to launch ultrasound Doppler operation. The transducer will scan depths at each element location to detect blood movement, i.e., Doppler power. If the Doppler power detection indicator 150 lights up, Doppler power in the frequency band of 300-1000 Hz representative of blood flow is detected that is of sufficient magnitude for concluding that a fetal or maternal heart beat can reliably be measured from arterial blood flow. The heart beat rate of the mother is usually lower than the fetal heart beat rate. In addition to the indicator 150, a short beep may be emitted from the audio speaker 144, to alert the user to the onset of detection of Doppler power. Alternatively or in addition, audio feedback of the Doppler signal may come over the audio speaker 144. The probe 100 is held in place for several seconds; if not, the Doppler power drops and a lit indicator light 150 must again be achieved. If, at the end of the several-second period, neither the fetal nor maternal heart beat is detected, the user can move the probe to another location on the mother's abdomen, and can do this repetitively until detection occurs. If the fetal or maternal heart beat is detected, i.e., a body vessel, and in particular an artery, is found, by the signal processing route 220-232, 240, 256, the corresponding fetal heart beat acquisition indicator 152 or maternal heart beat acquisition indicator 154 is lit (step S308). The user, repetitively, moves the probe 100 to a next location on the mother's abdomen until both indicators 152, 154 are lit (step S312), indicating that the pulse cycle time, a clinical Doppler parameter, has been acquired, and extracted, for both the mother and fetus.

The user now places the probe to check for normality/abnormality of blood flow in a corresponding maternal or fetal vessel which is the target vessel (step S316). If the Doppler power detection indicator 150 does not light up (step S320), Doppler power in the frequency band of 300-1000 Hz representative of blood flow is not detected or is of insufficient magnitude for finding one or more blood vessels. In that case, the user moves or tilts the probe 100 (step S324), until the indicator 150 is lit.

Once the indicator is lit, the probe 100 is held in place to process the volume of interest 106. Each element 126 will fire for a few heartbeats, for a total of 3 to 5 seconds, to obtain Doppler information within its footprint. This entails about 2 to 3 minutes of volumetric data acquisition, if the 32 elements 126 are operated one by one. To reduce the total time period, the elements 126 are operated in one or more groups, taking care that acoustic beams of the respective elements 126 do not significantly interfere and degrade the received data. Minimizing the total acquisition time reduces the possibility of errors due to patient or examiner movement during the acquisition period (step S328). Possible groupings are discussed in more detail further below.

Advantageously, the volumetric data acquisition occurs automatically and without need for user intervention. Since the display of an image of a blood vessel is not required, no electronic focusing of ultrasound is required. The device is thereby simplified and cost-effective.

The outcome of the processing may be a green light of the normal blood-flow indicator 156, a red light of the abnormal blood-flow indicator 158, or lack of either light if the blood vessel currently being examined does not match the target vessel. If neither indicator 156, 158 is lit (step S332), processing returns to step S324.

An example of the processing in step S328 is provided in FIG. 3B. A volume of interest 106, which would change each time the probe 100 is moved or tilted, but which is fixed while the user holds the probe steady, is subject to examination for blood vessels present. In particular, the Doppler power in a frequency band of 300-1000 Hz is computed. This generates a 3-dimensional (3D) representation of vessels 108-112 in the scan volume. The total number of vessels in the scan volume is identified using continuity criteria. For example, for the 8 immediately adjacent pixels, i.e., the 4 side and 4 diagonal pixels, it is assumed that adjacent pixels for which blood flow is detected represent the same blood vessel. Yet, the blood vessels can be mapped in 3D, since the transducer receive-gates can be set for different depths. In 3D, a least-squares based line-fitting algorithm is used to find the straight line joining the points identified using the continuity criterion. The angle of the straight line from the ultrasound-receiving faces 132 of the transducer elements 126 is then computed. This results in a 3D map from which individual vessels, and their individual orientations, are identifiable. With the orientations identified, spatial features can be determined from the map. For example, in a uterine artery scan the Doppler sample volume is typically placed at the pseudo-intersection of the uterine and iliac arteries. The intersection is determined as the location of the minimum sum of the squared distances between pixels on the vessels (step S336). Alternatively, the adjacency examined for the continuity criterion may be, instead of the 8 adjacent pixels in 2D, the 26 adjacent pixels in 3D.

If the vessel map contains no vessels 108-112 (step S340), processing of the current volume of interest 106 is complete, no diagnosis is rendered, and control proceeds to step S332.

Otherwise, if a vessel 108-112 is detected, a vessel from among those found in the volume of interest 106 is selected for fluid-flow analysis and as a candidate for matching the target vessel (step S344). Any criterion can be used for the selection, since selection of candidates does not end until the target vessel is found or all of the vessels 108-112 in the volume of interest 106 have been processed.

Information particular to the selected vessel is generated, as seen in FIG. 3B (step S348). The information includes spectral Doppler waveform characteristics (mean frequency estimate, cycle time—time interval between 2 successive peaks, spectral width—width between maximum and minimum frequency envelope at peaks and valleys), time to peak, holder's defect and clinical Doppler indices (such as, S/D, PI and RI), for example.

Based on the generated information and analysis thereof, the blood vessel classifier 200 classifies the selected vessel (step S352).

If the classification does not match the target vessel (step S356), and no next vessel from among those found in the volume of interest 106 exists (step S360), control proceeds to step S332.

Otherwise, if the classification does not match the target vessel, but a next vessel does exist, control branches back to step S344, with that next vessel serving as the selected vessel (step S364).

If, on the other hand, the classification matches the target vessel, the probe 100 draws a conclusion as to normality of the blood flow in the target, i.e., selected, vessel. In particular and by way of example, the Doppler parameters are compared with nomograms, i.e., tables representing the range of expected Doppler indices as a function of gestational age, to determine whether the flow profile is normal or abnormal. Optionally, before drawing a conclusion as to blood flow normality, further acquisition of Doppler data may occur (step S368).

Based on the conclusion, an indication as to normality of the blood flow in the selected vessel is provided by the green light of the normal blood-flow indicator 156 or the red light of the abnormal blood-flow indicator 158 (step S372).

Figures 4A, 4B, 4C:
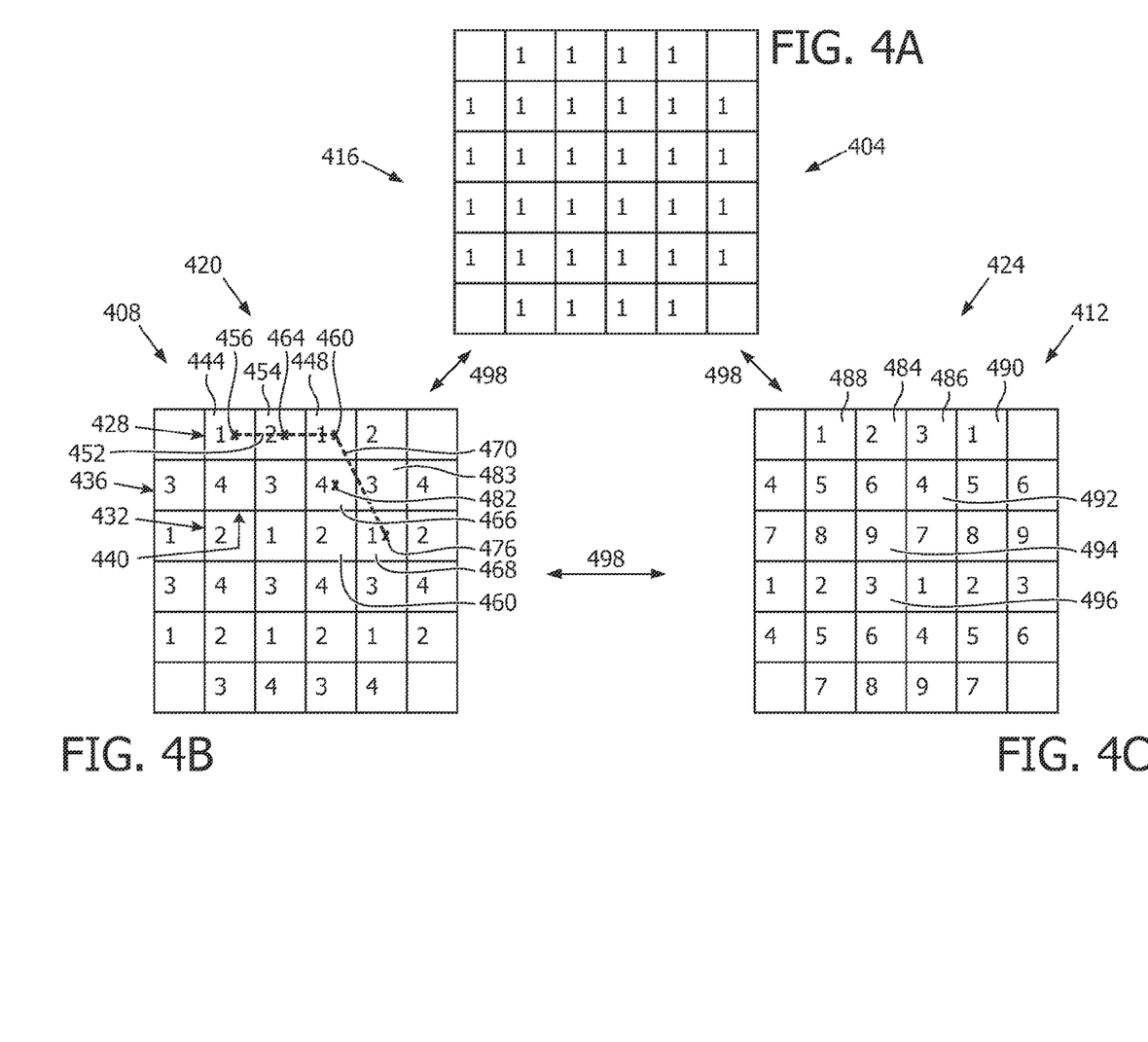
FIGS. 4A-4C are schematic diagrams of some of the possible spacing states, and excitation schemes, for a transducer array.

FIGS. 4A-4C illustrate exemplary spacing states 404, 408, 412, and excitation schemes 416, 420, 424, for the transducer array 124.

In the first spacing state 404, shown in FIG. 4A, the number of transducer elements 126 that intervene between elements of the same group is zero. In particular, only a single group exists, and the elements 126 of the group are arranged in immediate adjacency in the array 124. Accordingly, the degree of intra-group, element-to-element non-adjacency is zero. The elements 126, although imaging independently, are operated concurrently as a single group in imaging to produce the vessel map. The time period needed to acquire the data for creating the map is therefore relatively short, i.e., 3-5 seconds for each element and therefore 3-5 seconds total. This, as mentioned above, is advantageous, since there is less chance for imaging error caused by patient or examiner movement.

The first spacing state 404 is not always feasible. Acoustic cross-talk between elements 126, which is undesired, increases with increasing element-to-element adjacency in the array 124. In particular, there is the potential for an unacceptable amount of ultrasound received by an element 126 that was transmitted by a neighboring element.

However, the amount of cross-talk decreases with shallower vessels. It also decreases with smaller vessels, i.e., the interference effect is dependent on the size of the vessel being imaged and the size of the element 126.

In the second spacing state 408, shown in FIG. 4B, the number of transducer elements 126 that intervene between elements of a group is at least one. In other words, the at least two elements of a group are separated from one another by at least one respective element. The eight elements 126 denoted by the numeral "1" in FIG. 4B are in the same group, referred to hereinafter as the first group 428 for the second spacing state 408. A second group 432 for the second spacing state 408 is comprised of the eight elements 126 denoted by the numeral "2." Likewise, a third group 436, and a fourth group 440, of the second spacing state 408 are each respectively comprised of the eight elements 126 denoted by the numerals "3" and "4." The groups 428, 432, 436, 440 spatially overlap, while remaining element-wise distinct.

In the first group 428, although the same principle applies in the other groups 432, 436, 440 for this spacing state 408, any two adjacent elements 444, 448 of the group are separated by at least a minimum, predetermined distance 452.

This distance is represented in FIG. 4B by a broken line. The minimum distance 452, in some embodiments, is a nonzero degree of intra-group, element-to-element non-adjacency associated with the spacing state 408.

This is distinguishable from a zero degree of intra-group, element-to-element non-adjacency. An example of the latter would be a strict, two-group checkerboard pattern. Such a pattern would have zero adjacency, because the corners of intra-group elements meet. Nevertheless, it is noted that such a pattern would still come within the intended scope of the invention by virtue of the feature that groups 428, 432, 436, 440 mutually intermesh element-wise.

Element-to-element distance can be measured from the corresponding geometric centers 456, 460. The geometric center of an element face 132 can be calculated as follows. Conceptually, encase the face 132 in, as is the case, a two- or three-dimensional, fine, equal-celled grid. For each grid coordinate, e.g., "x" or "y", take the arithmetic mean over all cells coincident with the face 132.

The minimum distance 452 indicative of a nonzero degree of intra-group, element-to-element non-adjacency may be sufficient to allow some element of another group 432, 436, 440 to intervene between the pair of first group elements 444, 448, with the corresponding geometric centers 456, 460, 464 colinear. Here, the intervening element 454 belongs to the second group 432: although, if it is assumed in the present example that all elements are equally dimensioned, any element of a group other than the first group 428 could have been selected instead. The same value of the minimum distance 452 applies to all pairs of elements of the first group 428.

The non-adjacency for some, or most, of the element pairs of a group may be greater than the minimum degree for that group. This is the case, in the present example, by virtue, for instance, of the element pair 448, 468. As seen in FIG. 4B, the distance 470 here is measurable between the geometric centers 460, 476 of the faces 132 of the respective elements 448, 468. Hypothetically, by appropriately shifting rightward the intervening element 466, its geometric center 482 and those of the sandwiching elements 448, 468 would be made colinear, showing that the minimum distance 452 is sufficient. Alternatively, the intervening element 483 could, hypothetically, be shifted leftward to likewise accomplish colinearity of geometric centers. The minimum degree of non-adjacency is observed throughout the group, e.g., the first group 428. For the second spacing state 408, the elements of a given group are pair-wise separated by at least one respective intervening element of another group. As with all spacing states 404, 408, 412, only one group 428, 432, 436, 440 of the second spacing state 408 operates at any given time.

As mentioned above, imaging is performed time-wise in parallel using transducer elements of a current group, and time-wise sequentially by group. Thus, the elements 126 of the first group 428 are operated concurrently for a data acquisition period. Concurrent operation then shifts after each period to a subsequent group, i.e., to the second group 432, then the third group 436 and then the fourth group 440.

Due to the spacing in the array 124 between elements of the same group in the second spacing state 408, acoustic cross-talk is significantly less than what would occur in the first spacing state 404. In tradeoff, total vessel map acquisition time is quadrupled, since there are four groups 428, 432, 436, 440, in comparison to the single group in the first spacing state 404. However, this is still ⅛ the time required in the case of element-level sequential acquisition, i.e., separately for each of the 32 elements 126.

Under some conditions, even the spacing afforded by the second spacing state 408 may result in more cross-talk that can be tolerated without sacrificing clinical utility and accuracy. Thus, the third spacing state 412, with greater intra-group inter-element spacing may be needed.

In the third spacing state 412, shown in FIG. 4C, the minimum distance is, for the one or more pairs of the elements 126 of the current group, sufficient to allow some two elements of another one or more of the groups to collectively intervene between the pair, with the corresponding geometric centers colinear. Thus, for instance, two elements 484, 486 intervene between a pair 488, 490, each element of the pair being of the same group which is the first group for the third spacing state 412. The distance between the pair 488, 490 of elements is the minimum distance, i.e., the minimum, nonzero degree of element-to-element non-adjacency between elements of the first group for the third spacing state 412. Likewise, two elements 492, 494 intervene between a pair 486, 496 of elements of the same group which is here the third group; albeit, here, the intervening elements would hypothetically require shifting, i.e., leftward and rightward respectively, to bring all four geometric centers into alignment. Accordingly, as seen in FIG. 4C, the distance between the pair 486, 496 of elements is greater than the minimum distance.

The higher degree of element-to-element non-adjacency for the third spacing state 412, in comparison the first and second spacing states 404, 408 further mitigates, or reduces the likelihood of, any acoustic cross-talk among the elements 126. There are nine groups in the third spacing state 412, which still affords, in comparison to a purely sequential overall scheme, a substantial improvement in total data acquisition time.

From FIGS. 4B and 4C, it is seen that the groups are element-wise mutually exclusive, in that no element belongs to more than one group of a given spacing state 404, 408, 412.

It is also seen that the groups are spatially disposed with respect to each other so as to mutually intermesh element-wise. Their elements 126 collectively form a mesh. Accordingly, the required amount of purity in the Doppler signal is achieved while, at the same time, the ultrasound interface "real estate" is efficiently managed so as to be functional throughout. Although no spacing state in above-discussed embodiments requires an intra-group, element-to-element separation that exceeds two elements, such larger non-adjacency may be implemented, especially in the case of an array having relatively many elements. In designing which elements 126 are assigned to which groups 428, 432, 436, 440, the criteria for placing an element in a respective group may be based on Euclidean distance or combinatorial algorithms, e.g., n-wise algorithms such at AETG/Jenny™ may be employed. Use of such criteria in designing the grouping may occur before probe operation. Or it may occur during probe operation in order, for example, to work around a detected fault in an element 126. The probe may be configured for a single spacing state 404, 408, 412 or for transitioning 498 between two or more of them.

In the above-described embodiments, the elements 126 are in two-dimensional matrix array 124, although the array may be of fewer or more dimensions. Also, the array need not be in a matrix arrangement.

Nor are the element faces 132 restricted to any particular shape or size. It is within the intended scope of the invention too that the element faces 132 need not all be laterally dimensioned the same. Thus, the sufficiency criterion for the minimum inter-element distance for a group may be met, even if a selected element 126 requires a particular orientation to fit, i.e., intervene.

Within the probe 100, control circuitry (not shown), serving as the described ultrasound examination device, can take the form of one or more integrated circuits (ICs). One or more such ICs can, alternatively, be configured for installation into existing apparatus such as ultrasound Duplex scanners.

More generally, the described ultrasound examination device may be implemented as one or more integrated circuits, the control circuitry for the array 124, or as, by way of further example, an apparatus, such as the probe 100, that includes the control circuitry and the array 124.

A signal for operating the array 124 in accordance with the techniques proposed herein can be formed by varying an electrical current applied to a wire input to the array, or applied to an antenna for wireless transmission of the signal and reception by the probe 100.

Figure 5:
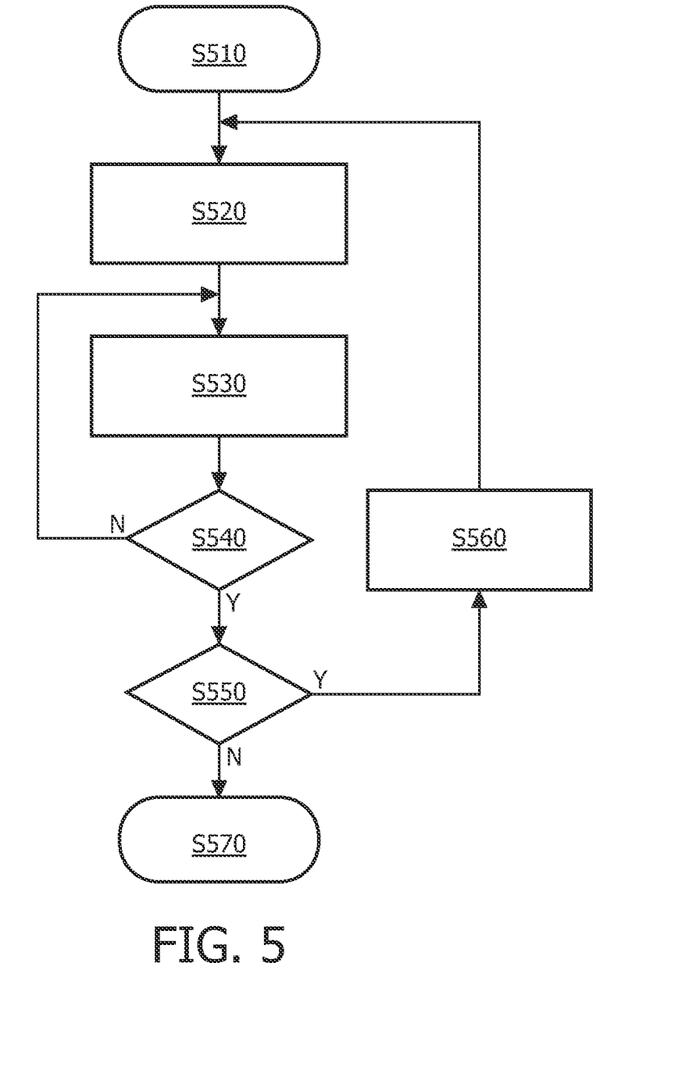
FIG. 5 is a flow chart of an exemplary excitation scheme.

FIG. 5 is a sample excitation scheme. To begin volumetric imaging (step S510), the elements 126 of the current group are fired simultaneously (step S520). Imaging continues without using elements 126 collectively to focus or steer a beam (step S530). When the data acquisition period expires (step S540), if a next group for the current spacing state 404, 408, 412, or only spacing state, exists (step S550), that next group is made the current group (step S560) and processing returns to step S520. Otherwise, if no next group exists (step S550), volumetric imaging is now complete (step S570).

In some implementations of the probe 100, merely a single spacing state is provided. If, for example, the probe 100 is to be used on a particular part of the anatomy, vessel size and depth may be known or relatively invariable. A particular spacing state may therefore be found empirically to be optimal.

In other implementations, the grouping 428, 432, 436, 440 of elements 126 can be varied, which entails transitioning 498 to a new spacing state 404, 408, 412. The regrouping may be automatic, based on preliminary data acquisition indicative of vessel size and/or vessel depth. Or it may occur in response to the clinician's actuation of controls.

Figure 6:
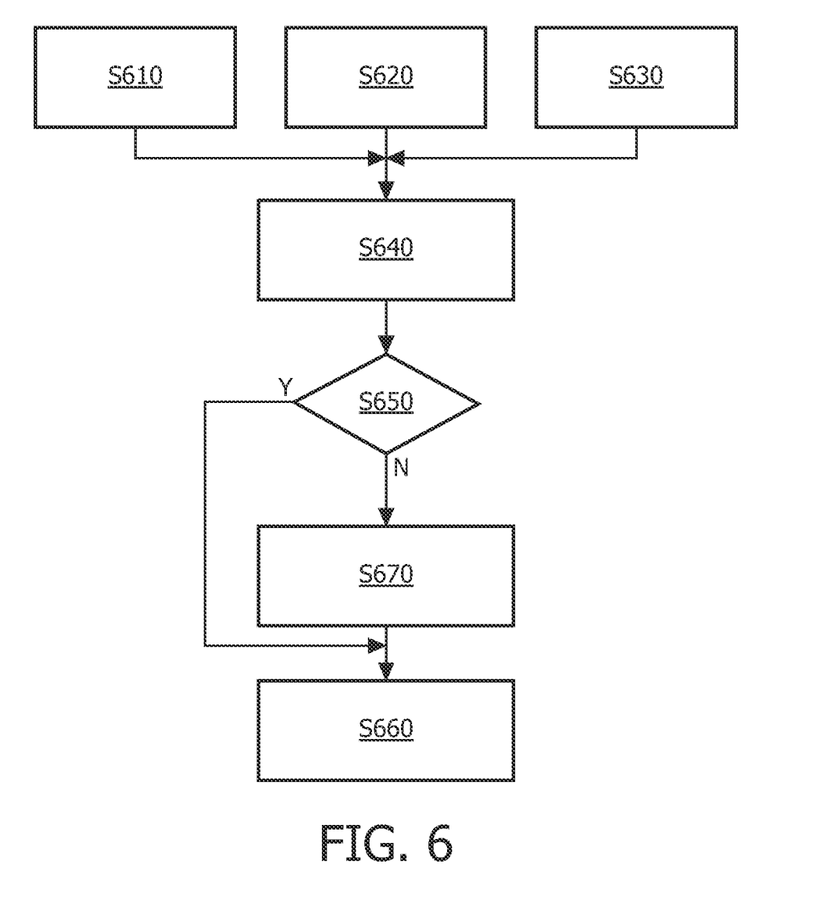
FIG. 6 is a flow chart exemplary of spacing state initialization.

FIG. 6 provides an example of spacing state initialization of a device 100 for which the grouping 428, 432, 436, 440 can be varied.

The clinician inputs an indication of total acquisition time (step S610), as part of the initialization in step S304. Alternatively, the input could be indicative of vessel size (step S620) and/or vessel depth (step S630), where the inputting merely selects a target blood vessel for examination in step S304 or instead involves entering a value for vessel size and/or vessel depth.

From the input, an appropriate grouping is determined (step S640).

If the current grouping matches the determined grouping (step S650), by default or due to the last used grouping, volumetric acquisition of Doppler signals commences (step S660) which coincides with step S510.

Otherwise, if there is no match (step S650), transition 498 is made to the spacing state 404, 408, 412 that corresponds to the determined grouping (step S670). In one configuration, the 32 transducer elements 126 are connected to 32 separate transmit/receive channels. Only the elements 126 of the current group are on. All other elements of the array 124 are off. Alternatively, the number of channels in the probe 100 can be reduced to the maximum number, over all groups, of elements 126 of a group 428, 432, 436, 440. For the second spacing state 408 in FIG. 4B, each of the groups 428, 432, 436, 440 has the same number of elements 126, i.e., eight; so, the maximum number of elements 126 is eight. The connections of the eight channels to respective elements 126 are switched with each transition of spacing state 404, 408, 412. This can be accomplished through the use of a cross-point switch operated by a field programmable gate array (FPGA). These devices are discussed in the commonly-assigned patent U.S. Pat. No. 5,997,479 to Savord et al., entitled "Phased Array Acoustic Systems With Intra-Group Processors" and the commonly-assigned patent application US2010/0277305 to Garner et al., entitled "Wireless Ultrasound Probe Asset Tracking." A control program, in software and firmware for example, can set up the appropriate connections between the channels and the transducer elements 126 for a given group according to a pre-loaded scan sequence look up table. Once the transition 498 is made to the determined spacing state, 404, 408, 412, volumetric acquisition can begin at step S510.

The novel excitation schemes proposed herein reduce the examination time length, thereby avoiding the error from movement by the patient or the clinician that might otherwise occur. In addition, the number of receive/transmit channels can be reduced to largest element count of any group. This lowers the cost of manufacture, which likewise is one of the motivating factors for creating a relatively simple, self-contained device 100 with relatively few transducer elements 126. By judicious choice of a spacing scheme, the ill effects of cross-talk can be eliminated or mitigated; yet, the intermeshing of element groups makes efficient use of the probe face "real estate," resulting in a small form factor. By not implementing electronic focusing or steering, the device 100 is further simplified and made cost-efficient. The automatic Doppler analysis relieves the need for a displayable image and a person trained for interpreting such a display. The automatic nature retains reliability and may even improve it. By making examination faster, workload is relieved. Since the medical diagnostic device 100 is relatively inexpensive, it can be made more widely available.

A device images time-wise in parallel using transducer elements of a group. In some embodiments, the elements are of a current group and imaging is time-wise sequential by group. The groups may be spatially disposed with respect to each other so as to mutually intermesh element-wise. The imaging may include volumetric imaging. The device can be configured for not collectively using any of the elements to focus, nor to steer, a beam used in the imaging. The device might be operable to transition between spacing states at least one of which is characterized by a respective minimum, nonzero, degree of intra-group, element-to-element non-adjacency, or may be fixed at one spacing state. The transitioning may be automatic, in response to input indicative of blood vessel size and/or depth.

Although methodology of the present invention can advantageously be applied in providing medical diagnosis for a human or animal subject, the scope of the present invention is not so limited. More broadly, techniques disclosed herein are directed to efficiently finding, and subjecting to fluid-flow analysis, vessels in body tissue, in vivo, in vitro or ex vivo.

What is proposed herein pertains to transducer element firing schemes for an automated Doppler device for rendering a clinical diagnosis based on a result of analyzing the characteristics of spectral Doppler waveforms. Applications include carotid and renal arteries screening, ABI measurements for detecting peripheral arterial disease (PAD), tran-scranial, bleed detection in trauma or other hemorrhages in addition to fetal well-being assessment.

While the invention has been illustrated and described in detail in the drawings and foregoing description, such illustration and description are to be considered illustrative or exemplary and not restrictive; the invention is not limited to the disclosed embodiments.

For example, in a given spacing state, the minimum distance between geometric centers may vary by group. Also, although the novel firing schemes are described for a two-dimensional array of transducers, the array may be multi-dimensional or in particular geometric arrangement.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. An ultrasound device comprising:
an array of transducer elements for apportioning transducer elements of the array of transducer elements into a plurality of groups for operation by group; and
a processor configured to control operation of the array of transducer elements, based on said apportioning, for imaging time-wise in parallel using the transducer elements of the array of transducer elements of a current group of said plurality of groups, and time-wise sequentially by group, the plurality of groups being spatially disposed with respect to each other so as to intermesh element-wise, wherein each of said plurality of groups comprises only non-adjacent transducer elements apportioned in accordance with a spacing state in which for all pairs of transducer elements of a first group of the plurality of groups, one or more transducer elements of one or more other groups of the plurality of groups intervene between the two transducer elements of the pair of transducer elements, and wherein each transducer element of the array of transducer elements has a face with a geometric center, and wherein the transducer elements of the array of transducer elements are arranged such that a line passing through the geometric centers of at least some of the transducer elements of one group of the plurality of groups does not fully enclose the transducer elements of any other group in the plurality of groups,
wherein the processor is configured to control the operation of the array for the imaging time-wise in parallel by operating said transducer elements of said current group of said plurality of groups to, in a non-phased manner, image independently.

2. The ultrasound device of claim 1, being configured for medical-image acquisition, and for imaging via said operation to form a map of blood vessels, said array of transducer elements comprising a non-phased array for said operation, said processor being configured not to collectively use any of said transducer elements of said one or more other groups of the plurality of groups to focus, nor to steer, a beam used in said imaging.

3. The ultrasound device of claim 1, wherein the processor is configured to cause imaging via a transducer element of said current group, said processor being further configured to detect blood flow at a pixel based on Doppler information received from the transducer element, wherein the pixel spatially corresponds to the transducer element, and based on a result of said blood flow, deciding between presence or non-presence of a blood vessel with respect to said pixel.

4. The ultrasound device of claim 1, said processor being further configured for varying grouping of the transducer elements.

5. The ultrasound device of claim 4, said processor being further configured for analyzing the imaging and for performing said varying based on a result of said analyzing.

6. The ultrasound device of claim 4, said varying comprising transitioning between one and another of at least two spacing states of the plurality of spacing states, at least one of which is characterized by a respective minimum, nonzero, degree of element-to-element non-adjacency between transducer elements of a group.

7. The ultrasound device of claim 6, wherein the processor is configured for medical-image acquisition and for said transitioning automatically in response to input indicative of at least one of a blood vessel size and a blood vessel depth.

8. The ultrasound device of claim 1, wherein the distance between the pair of transducer elements provides a minimum, nonzero, degree of element-to-element non-adjacency between the transducer elements of said current group, said minimum representative of a minimum distance between said geometric centers.

9. The ultrasound device of claim 1, said plurality of groups being element-wise mutually exclusive.

10. The ultrasound device of claim 1, the imaging comprising medical imaging, said ultrasound device configured for said operation based on said apportioning among more than one of said plurality of groups.

11. The ultrasound device of claim 1, wherein the array of transducer elements and the processor are enclosed within a housing of a handheld, stand-alone, diagnostic apparatus comprising said ultrasound device.

12. The ultrasound device of claim 11, further comprising one or more indicators provided on the housing, and wherein the one or more indicators are configured to provide a Doppler power detection indication, a fetal heartbeat acquisition indication, a maternal heartbeat acquisition indication, a normal blood-flow indication, an abnormal blood-flow indication, or a combination thereof.

13. The ultrasound device of claim 1, wherein the processor is further configured to select a spacing state from among a plurality of spacing states of the array of transducer elements including the groups of the plurality of groups, the plurality of spacing states including a second spacing state with at least three groups of transducer elements arranged such that, for all pairs of transducer elements of a first group, a distance between two transducer elements of each of the pairs of transducer elements of the first group allows two transducer elements of other groups of the at least three groups to intervene between the two transducer elements of the first group.

14. A non-transitory computer readable medium comprising computer instructions for operation of an ultrasound imaging device comprising an array of transducer elements, transducer elements of the array of transducer elements are grouped into groups of multiple ones of said transducer elements, said instructions, when executed by a processor, configure the processor to perform acts including:

control operation of said array of transducer elements for imaging via said array of transducer elements, time-wise in parallel using transducer elements of a current one of said groups of multiple ones of said transducer elements, and time-wise sequentially by group, said imaging being performed element-wise independently, the groups of multiple ones of said transducer elements being, pairwise, spatially disposed with respect to each other so as to intermesh element wise, wherein each of said groups of multiple ones of said transducer elements comprises only non-adjacent transducer elements grouped in accordance with a spacing state in which for all pairs of transducer elements of a first group of the groups of multiple ones of said transducer elements, one or more transducer elements of one or more other groups of multiple ones of said transducer elements intervene between the two transducer elements of the pair of transducer elements, and wherein each transducer element of the array of transducer elements has a face with a geometric center, and wherein the transducer elements of the array of transducer elements are arranged such that a line passing through the geometric centers of at least some of the transducer elements of one group of the groups of multiple ones of said transducer elements does not fully enclose the transducer elements of any other group in the groups of multiple ones of said transducer elements.

15. The non-transitory computer readable medium of claim 14, further comprising computer instructions to select a spacing state from among a plurality of spacing states of the array of transducer elements including the groups of multiple ones of said transducer elements, the plurality of spacing states including a spacing state with at least three groups of transducer elements arranged such that, for all pairs of transducer elements of a first group, a distance between two transducer elements of each of the pairs of transducer elements of the first group allows two transducer elements of other groups of the at least three groups to intervene between the two transducer elements of the first group.

16. A method of operating an ultrasound imaging device comprising an array of transducer elements, the transducer elements of the array of transducer elements are grouped into groups of multiple ones of said transducer elements, the method comprising acts including:

controlling by a processor operation of said array of transducer elements for imaging via said array, time-wise in parallel using transducer elements of a current one of said groups of multiple ones of said transducer elements, and time-wise sequentially by group, said imaging being performed element-wise independently, the groups of multiple ones of said transducer elements being, pair-wise, spatially disposed with respect to each other so as to intermesh element-wise, wherein each of said groups of multiple ones of said transducer elements comprises only non-adjacent transducer elements grouped in accordance with a spacing state in which for all pairs of transducer elements of a first group of the groups of multiple ones of said transducer elements, one or more transducer elements of one or more other groups of groups of multiple ones of said transducer elements intervene between the two transducer elements of the pair of transducer elements, and wherein each transducer element of the array of transducer elements has a face with a geometric center, and wherein the transducer elements of the array of transducer elements are arranged such that a line passing through the geometric centers of at least some of the transducer elements of one group of the groups of multiple ones of said transducer elements does not fully enclose the transducer elements of any other group in the groups of multiple ones of said transducer elements.

17. The method of claim 16, further comprising selecting by the processor a spacing state from among a plurality of spacing states of the array of transducer elements including the groups of multiple ones of said transducer elements, the plurality of spacing states including a spacing state with at least three groups of transducer elements arranged such that, for all pairs of transducer elements of a first group, a distance between two transducer elements of each of the pairs of transducer elements of the first group allows two transducer elements of other groups of the at least three groups to intervene between the two transducer elements of the first group.

* * * * *